United States Patent
Kuga (10) Patent No.: US 12,340,507 B2
(45) Date of Patent: Jun. 24, 2025

(54) ULTRASONIC DIAGNOSIS APPARATUS, IMAGE PROCESSING APPARATUS, METHOD, AND NON-TRANSITORY COMPUTER-READABLE STORAGE MEDIUM THAT GENERATE A RENDERING IMAGE OF THREE-DIMENSIONAL DATA USING A VALUE OF COLOR ATTENUATION

(71) Applicant: Canon Medical Systems Corporation, Otawara (JP)

(72) Inventor: Itsuki Kuga, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 532 days.

(21) Appl. No.: 17/658,476

(22) Filed: Apr. 8, 2022

(65) Prior Publication Data

US 2022/0327697 A1 Oct. 13, 2022

(30) Foreign Application Priority Data

Apr. 13, 2021 (JP) ................................ 2021-067854

(51) Int. Cl.
*G06T 7/00* (2017.01)
*A61B 8/14* (2006.01)
*G06T 7/90* (2017.01)

(52) U.S. Cl.
CPC .............. *G06T 7/0012* (2013.01); *A61B 8/14* (2013.01); *G06T 7/90* (2017.01); *G06T 2207/10136* (2013.01)

(58) Field of Classification Search
CPC .... G06T 7/90; G06T 2207/10136; A61B 8/14
USPC ........................................................ 382/128
See application file for complete search history.

(56) References Cited

U.S. PATENT DOCUMENTS

| 10,762,693 B2 | 9/2020 | Wahrenberg |
| 12,016,730 B2 * | 6/2024 | Huang ................. A61B 8/463 |
| 2015/0071516 A1 | 3/2015 | Kim |
| 2015/0154790 A1 | 6/2015 | Kim |
| 2016/0143623 A1 | 5/2016 | Schroecker et al. |

FOREIGN PATENT DOCUMENTS

| JP | 2016-135252 A | 7/2016 |
| JP | 2019-181168 A | 10/2019 |

OTHER PUBLICATIONS

Extended European Search Report issued on Sep. 2, 2022 in European Patent Application No. 22167912.9, 7 pages.
Japanese Office Action issued Sep. 3, 2024 in Japanese Patent Application No. 2021-067854, 5 pages.

* cited by examiner

*Primary Examiner* — Gabriel I Garcia
(74) *Attorney, Agent, or Firm* — Oblon, McClelland, Maier & Neustadt, L.L.P.

(57) ABSTRACT

According to one embodiment, an ultrasonic diagnosis apparatus includes processing circuitry. The processing circuitry generates three-dimensional data based on an echo reflection intensity acquired through a probe, acquires a plurality of parameters including base color parameters, and the three-dimensional data, and generates a rendering image of the three-dimensional data using a value of color attenuation taking account of propagation of light based on the echo reflection intensity and using the base color parameters.

14 Claims, 9 Drawing Sheets

ULTRASONIC DIAGNOSIS APPARATUS, IMAGE PROCESSING APPARATUS, METHOD, AND NON-TRANSITORY COMPUTER-READABLE STORAGE MEDIUM THAT GENERATE A RENDERING IMAGE OF THREE-DIMENSIONAL DATA USING A VALUE OF COLOR ATTENUATION

CROSS-REFERENCE TO RELATED APPLICATIONS

This application is based upon and claims the benefit of priority from Japanese Patent Application No. 2021-067854, filed Apr. 13, 2021, the entire contents of which are incorporated herein by reference.

FIELD

Embodiments described herein relate generally to an ultrasonic diagnosis apparatus, an image processing apparatus, a method, and a non-transitory computer-readable storage medium.

BACKGROUND

A technique for obtaining an echo reflection intensity of ultrasonic waves as three-dimensional data by an ultrasonic diagnosis apparatus and generating a rendering image is known. Recently, rendering image generation based on global illumination, which is a rendering method taking into account a light source and shading, is also carried out. When rendering is performed by this method, in computed tomography (CT) or magnetic resonance imaging (MRI), data acquired by each device is associated with a clinical tissue site. Colors, such as an environmental light color, a reflection color, and an attenuation color, are designated for data to perform rendering. In contrast, in an ultrasonic diagnosis apparatus, since an echo reflection intensity and a clinical tissue site are not associated with each other, colors cannot be designated for the echo reflection intensity, unlike in CT or MRI. Therefore, the ultrasonic diagnosis apparatus requires a coloring technique different from that used in CT or MRI.

Furthermore, in the ultrasonic diagnosis apparatus, since a rendering image is displayed in real time while a scan is performed, it is desirable to suppress the calculation load, and reflection and attenuation of optical properties are representatively used to designate colors. When the kinds of optical properties to be calculated are increased, generation of a naturally rendered image is expected, but this causes various problems; for example, setting of colors becomes complicated, the calculation load becomes heavy, and high-performance hardware is needed.

Conventionally, when global illumination rendering is performed with only reflection and attenuation, methods as described below are used; however, they each have problems. One method is to allocate a single reflection color and a single attenuation color to echo reflection intensities of a threshold or higher for a target of observation. This method has a problem in that when a light source is located near to the front of the target of observation, a clear shadow does not appear on the image; therefore, the overall image is expressed with a single color, in which case the visibility of an outline may be extremely low. Another method is to change a reflection color in association with the level of the echo reflection intensity to draw an outline. However, this method has a problem in that when the light source is moved, the color does not change and the outline is continuously drawn, in which case the stereoscopic effect and reality may be deteriorated. Under the circumstances, there is a demand for generating a natural rendering image without increasing the calculation load.

DETAILED DESCRIPTION

In general, according to one embodiment, an ultrasonic diagnosis apparatus includes processing circuitry. The processing circuitry generates three-dimensional data based on an echo reflection intensity acquired through a probe, acquires a plurality of parameters including base color parameters, and the three-dimensional data, and generates a rendering image of the three-dimensional data using a value of color attenuation taking account of propagation of light based on the echo reflection intensity and using the base color parameters.

Hereinafter, embodiments of the ultrasonic diagnosis apparatus will be explained in detail with reference to the accompanying drawings.

First Embodiment

Figure 1:
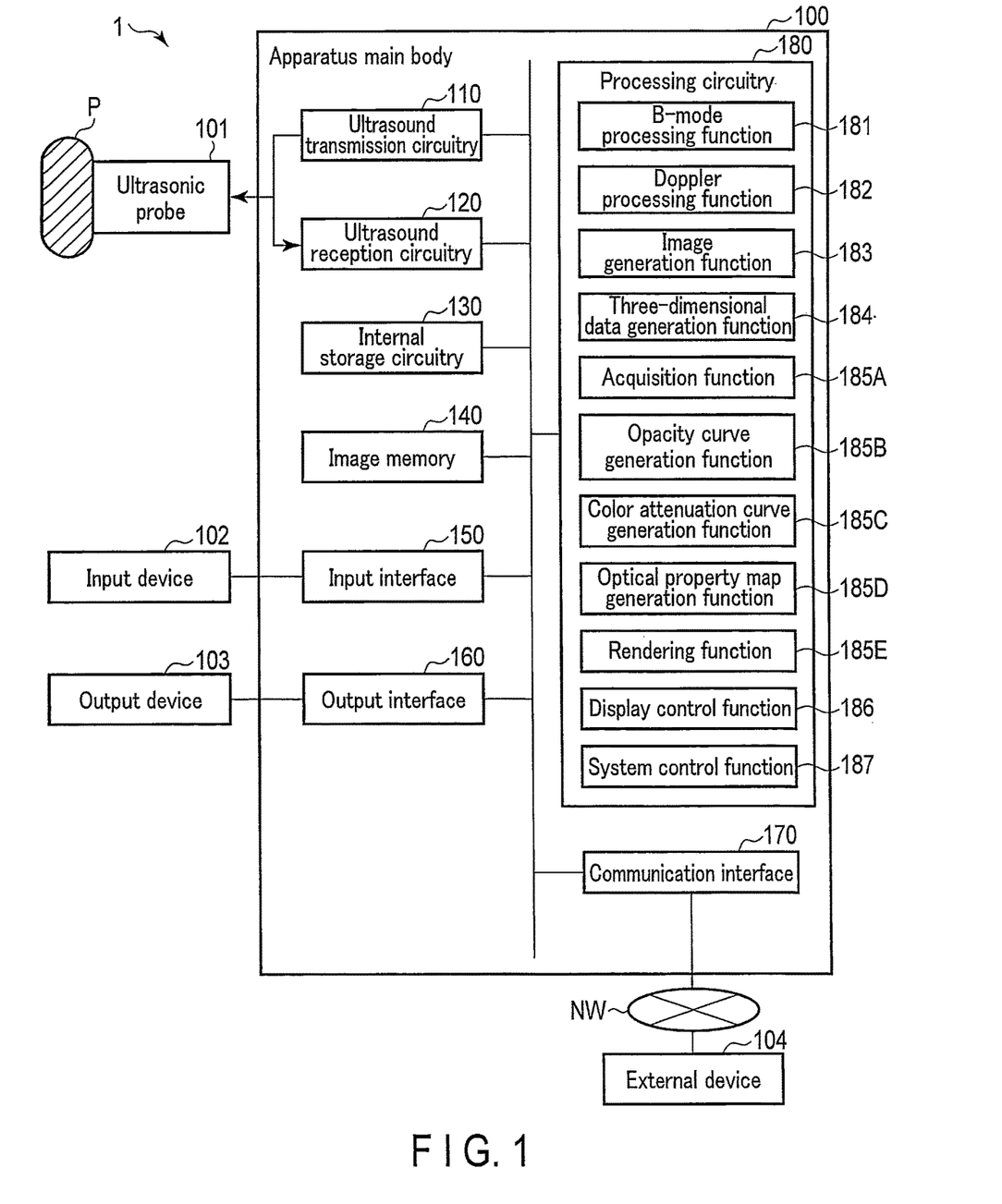
FIG. 1 is a block diagram showing a configuration example of an ultrasonic diagnosis apparatus according to a first embodiment.

FIG. 1 is a block diagram showing a configuration example of an ultrasonic diagnosis apparatus according to the first embodiment. The ultrasonic diagnosis apparatus 1 shown in FIG. 1 includes an apparatus main body 100 and an ultrasonic probe 101. The apparatus main body 100 is connected to an input device 102 and an output device 103. The apparatus main body 100 is connected to an external device 104 via a network NW. The external device 104 is a server including, for example, picture archiving and communication systems (PACS).

The ultrasonic probe 101 performs ultrasonic scanning in a scan area of a living body P, which is a subject, under the control of, for example, the apparatus main body 100. The ultrasonic probe 101 includes, for example, a plurality of piezoelectric transducers, a matching layer provided between a case and each of the piezoelectric transducers, and a backing material that prevents ultrasonic waves from propagating backward with respect to a direction of radiation from the piezoelectric transducers. The ultrasonic probe 101 is a two-dimensional array probe in which a plurality of ultrasonic transducers are aligned along, for example, a first element alignment direction (elevation direction) and a second element alignment direction (azimuth direction). The ultrasonic probe 101 is detachably connected to the apparatus main body 100. The ultrasonic probe 101 may be provided with a button which is to be depressed in an offset process or an operation for freezing ultrasonic images (freeze operation) or the like.

The piezoelectric transducers generate ultrasonic waves in response to a drive signal supplied from ultrasound transmission circuitry 110 included in the apparatus main body 100. An ultrasonic wave is thereby transmitted from the ultrasonic probe 101 to the living body P. When the ultrasonic wave is transmitted from the ultrasonic probe 101 to the living body P, the transmitted ultrasonic wave is sequentially reflected on the acoustic impedance discontinuous surfaces of the body tissue of the living body P, and is received as a reflection wave signal by the plurality of piezoelectric transducers. The amplitude of a received reflection wave signal depends on the difference in acoustic impedance on the discontinuous surfaces from which the ultrasonic wave is reflected. If the transmitted ultrasonic pulse is reflected from the surface of, for example, a moving bloodstream or a cardiac wall, the frequency of the resultant reflection wave signal will be shifted due to the Doppler effect, with the shift depending on the velocity component in the ultrasonic transmission direction of the moving object. The ultrasonic probe 101 receives the reflection wave signal from the living body P, and converts it into an electric signal.

FIG. 1 illustrates a connection relationship between the ultrasonic probe 101 and the apparatus main body 100. However, a plurality of ultrasonic probes may be connected to the apparatus main body 100. Which of the connected ultrasonic probes is to be used for the ultrasonic scanning can be selected freely through, for example, a software button on a touch panel (to be described later).

The apparatus main body 100 is an apparatus that generates an ultrasonic image based on the reflection wave signal received by the ultrasonic probe 101. The apparatus main body 100 includes the ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasonic probe 101. The ultrasound transmission circuitry 110 is realized by, for example, a trigger generation circuit, a delay circuit, and a pulsar circuit. The trigger generation circuit repeatedly generates rate pulses for forming transmission ultrasonic waves at a predetermined rate frequency. The delay circuit gives a delay time for each piezoelectric transducer to each rate pulse generated by the trigger generation circuit. This delay time is required to converge the ultrasonic wave generated from the ultrasonic probe into a beam and determine the transmission directivity. The pulsar circuit applies a drive signal (drive pulse) to a plurality of ultrasonic transducers of the ultrasonic probe 101 at the timing based on a rate pulse. By varying the delay time provided to each rate pulse by the delay circuit, the transmission direction from the surfaces of the piezoelectric transducers can be freely adjusted.

The ultrasound transmission circuitry 110 can freely change the output intensity of an ultrasonic wave by the drive signal. In the ultrasonic diagnosis apparatus, the influence of attenuation of ultrasonic waves in the living body P can be reduced by increasing the output intensity. In a reception time, a reflection wave signal with a high S/N ratio can be acquired by the ultrasonic diagnosis apparatus by reducing the influence of attenuation of ultrasonic waves.

Generally, when an ultrasonic wave propagates in the living body P, the intensity of ultrasonic vibrations (also called sound power) corresponding to the output intensity is attenuated. The attenuation of sound power is caused by absorption, scattering, reflection, etc. The degree of attenuation of the sound power depends on the frequency of the ultrasonic wave and the distance in radial direction of the ultrasonic wave. For example, the degree of attenuation is increased by increasing the frequency of the ultrasonic wave. Further, the degree of attenuation is increased as the distance in radial direction of the ultrasonic wave becomes longer.

The ultrasound reception circuitry 120 is a processor that performs various processes on the reflection wave signal received by the ultrasonic probe 101 and thereby generates a reception signal. The ultrasound reception circuitry 120 generates a reception signal based on the reflection wave signal of the ultrasonic wave acquired by the ultrasonic probe 101. Specifically, the ultrasound reception circuitry 120 is realized by, for example, a preamplifier, an A/D converter, a demodulator, and a beam former. The preamplifier performs gain correction processing by amplifying the reflection wave signal received by the ultrasonic probe 101 for each channel. The A/D converter converts the gain-corrected reflection wave signal into a digital signal. The demodulator demodulates the digital signal. The beam former provides the demodulated digital signal with delay time required to determine the reception directivity, and adds the digital signals to which delay time is provided. By the addition process of the beam former, a reception signal with an enhanced reflected component in a direction corresponding to the reception directivity is generated. Hereinafter, "the reflection wave signal of the ultrasonic wave" and "the reception signal" are collectively called "the echo signal". Therefore, "the intensity of the reception signal" may be reworded to "the intensity of reflection of the echo signal (the echo reflection intensity)".

The internal storage circuitry 130 includes a processor-readable storage medium, such as a magnetic storage medium, an optical storage medium, or a semiconductor memory. The internal storage circuitry 130 stores therein a program for realizing ultrasonic transmission/reception, a program relating to global illumination (GI) image generation processing (to be described later), various data, etc. The programs and various data may be pre-stored in the internal storage circuitry 130. Alternatively, the programs and various data may be stored and distributed in a non-transitory storage medium, read from the non-transitory storage medium and installed in the internal storage circuitry 130. The internal storage circuitry 130 stores B-mode image data, contrast image data, image data relating to bloodstream visualization, three-dimensional data, etc. generated by the processing circuitry 180, in accordance with an operation that is input via the input interface 150. The internal storage circuitry 130 can transfer the stored image data and three-dimensional data to the external device 104 or the like via the communication interface 170.

The internal storage circuitry 130 may be a drive etc. which reads and writes various types of information to and from a portable storage medium, such as a CD drive, a DVD drive, and a flash memory. The internal storage circuitry 130 may write the stored data onto a portable storage medium to store the data into the external device 104 by way of the portable storage medium.

The image memory 140 includes a processor-readable storage medium, such as a magnetic storage medium, an optical storage medium, or a semiconductor memory. The image memory 140 stores image data items corresponding to a plurality of frames immediately before a freeze operation input via the input interface 150. The image data stored in the image memory 140 is, for example, continuously displayed (cine-displayed). The image memory 140 may store not only the image data but also three-dimensional data.

The internal storage circuitry 130 and the image memory 140 are not necessarily implemented by independent storage devices. The internal storage circuitry 130 and the image memory 140 may be implemented by a single storage device. Each of the internal storage circuitry 130 and the image memory 140 may be implemented by a plurality of storage devices.

The input interface 150 receives various instructions from an operator through the input device 102. The input device 102 is, for example, a mouse, a keyboard, a panel switch, a slider switch, a trackball, a rotary encoder, an operation panel, or a touch panel. The input interface 150 is coupled to the processing circuitry 180 via a bus, for example, so that it can convert an operation instruction that is input by the operator, to an electric signal, and output the electric signal to the processing circuitry 180. The input interface 150 is not limited to physical operation components such as a mouse and a keyboard. For example, the input interface may include circuitry which receives an electric signal corresponding to an operation instruction input from an external input device provided independently from the ultrasonic diagnosis apparatus 1, and outputs the electric signal to the processing circuitry 180.

The output interface 160 is an interface to output, for example, the electric signal from the processing circuitry 180 to the output device 103. The output device 103 may be any display such as a liquid crystal display, an organic EL display, an LED display, a plasma display, or a CRT display. The output device 103 may be a touch-panel display that also serves as the input device 102. The output device 103 may also include a speaker configured to output a voice in addition to the display. The output interface 160 is connected to the processing circuitry 180, for example, via a bus, and outputs the electric signal coming from the processing circuitry 180 to the output device 103.

The communication interface 170 is connected to the external device 104 via, for example, the network NW, and performs data communication with the external device 104.

The processing circuitry 180 is a processor acting as a nerve center of the ultrasonic diagnosis apparatus 1, for example. The processing circuitry 180 executes the programs stored in the internal storage circuitry 130, thereby realizing the functions corresponding to the programs. The processing circuitry 180 includes, for example, a B-mode processing function 181, a Doppler processing function 182, an image generation function 183, a three-dimensional data generation function 184 (three-dimensional data generation portion), an acquisition function 185A (acquisition portion), an opacity curve generation function 185B, a color attenuation curve generation function 185C (color attenuation curve generation portion), an optical property map generation function 185D (optical property map generation portion), a rendering function 185E (rendering portion), a display control function 186 (display control portion), and a system control function 187. Since the Doppler processing function 182 has a low relevance to the embodiment, it may be omitted from the functions of the processing circuitry 180.

The B-mode processing function 181 is a function of generating B-mode data based on the reception signals (echo signals) received from the ultrasound reception circuitry 120. In the B-mode processing function 181, the processing circuitry 180 performs an envelope detection process, a logarithmic compression process, or the like on a reception signal received from the ultrasound reception circuitry 120 to generate data (B-mode data) that expresses a signal intensity of the reception signal (echo reflection intensity) by a value of brightness (brightness value). The generated B-mode data is stored in a raw data memory (not shown in the drawings) as B-mode raw data on a two-dimensional ultrasonic scanning line (raster).

Furthermore, the processing circuitry 180 can perform harmonic imaging by the B-mode processing function 181. The harmonic imaging is an imaging method that utilizes not only a fundamental wave component but also a harmonic wave component (harmonic component) included in the reflection wave signal of the ultrasonic wave. The harmonic imaging includes, for example, a tissue harmonic imaging (THI) not using a contrast agent and a contrast harmonic imaging (CHI) using a contrast agent.

In the THI, a harmonic component can be extracted by using an amplitude modulation (AM) method, a phase modulation (PM) method, or an imaging method called an AMPM method, which is a combination of the AM method and the PM method.

With the AM method, the PM method, or the AMPM method, ultrasound wave transmission is performed more than once for a single scanning line, with different amplitudes and/or phases. Through the above processing, the ultrasound reception circuitry 120 generates a plurality of pieces of reflection wave data for each scanning line, and outputs the generated reflection wave data. The processing circuitry 180, by the B-mode processing function 181, performs addition and subtraction on the plurality of pieces of reflection wave data for each scanning line in accordance with a selected modulation method, thereby extracting a harmonic component. Furthermore, the processing circuitry 180 performs the envelope detection process or the like on the reflection wave data of the harmonic component, thereby generating B-mode data.

In the CHI, a harmonic component is extracted using, for example, a frequency filter. By the B-mode processing function 181, the processing circuitry 180 can separate reflection wave data (a harmonic component) whose reflection source is the contrast agent and reflection wave data (a fundamental wave component) whose reflection source is a living tissue in the living body P. As a result, the processing circuitry 180 can select a harmonic component from the contrast agent using a filter, thereby generating B-mode data to generate contrast image data.

The B-mode data used to generate contrast image data is data expressing an echo reflection intensity of the wave, whose reflection source is the contrast agent, as a brightness value. The processing circuitry 180 can also extract a fundamental wave component from the reflection wave data of the living body P, thereby generating B-mode data to generate living tissue image data.

The Doppler processing function 182 is a function of generating, by analyzing the frequencies of the reception signals received from the ultrasound reception circuitry 120, data (Doppler information) obtained by extracting motion information of a moving object in the region of interest (ROI) that is set in a scan area, based on the Doppler effect. The generated Doppler information is stored in a raw data memory (not shown in the drawings) as Doppler raw data (also called Doppler data) on a two-dimensional ultrasonic scanning line.

Specifically, by the Doppler processing function 182, the processing circuitry 180 estimates as the motion information of the moving object an average velocity, an average dispersion value, an average power value, etc. at each of a plurality of sampling positions, and generates Doppler data indicating the estimated motion information. The moving object is, for example, a bloodstream, cardiac tissue such as a wall of a heart, or a contrast agent. The processing circuitry 180 according to the present embodiment estimates, by the Doppler processing function 182, an average bloodstream velocity, a dispersion value of the bloodstream velocity, a power value of a bloodstream signal as motion information of the bloodstream (bloodstream information) at each of the sampling positions, and generates Doppler data indicating the estimated bloodstream information.

The image generation function 183 is a function of generating B-mode image data based on the data generated by the B-mode processing function 181. The processing circuitry 180, in the image generation function 183, converts (scan-converts) a scanning line signal sequence of ultrasonic scanning into, for example, a scanning line signal sequence in a video format representatively used by a television, etc. to generate image data for display (display image data). Specifically, the processing circuitry 180 executes RAW-pixel conversion relative to B-mode RAW data stored in the RAW data memory, for example, executes coordinate conversion corresponding to the ultrasonic scan state by the ultrasonic probe 101, to generate two-dimensional B-mode image data (also referred to as ultrasonic image data) constituted by pixels. In other words, by the image generation function 183, the processing circuitry 180 generates a plurality of ultrasonic images (medical images) respectively corresponding to a plurality of consecutive frames by transmission and reception of ultrasonic waves.

The processing circuitry 180 performs, for example, a RAW-pixel conversion on the Doppler raw data stored in the raw data memory so as to generate Doppler image data in which bloodstream information is visualized. The Doppler image data is one of average velocity image data, dispersion image data, and power image data, or image data obtained by a combination thereof. The processing circuitry 180 generates, as Doppler image data, color Doppler image data indicating bloodstream information in colors and gray-scale Doppler image data indicating a piece of bloodstream information as waveforms with a gray scale.

The three-dimensional data generation function 184 is a function of generating three-dimensional B-mode data (three-dimensional data) based on the reception signal received from the ultrasound reception circuitry 120. In the three-dimensional data generation function 184, the processing circuitry 180 allocates a brightness value to a voxel located in a three-dimensional space using the B-mode data generated by the B-mode processing function 181, thereby generating three-dimensional data. The three-dimensional data may be called volume data. Since the brightness value corresponds to the echo reflection intensity, it can be construed that the echo reflection intensity is allocated to the voxel of volume data. Therefore, "the brightness value of volume data" may be used in substantially the same meaning as "the echo reflection intensity".

The acquisition function 185A is a function of acquiring data relating to GI image generation processing, which will be described later. Specifically, by the acquisition function 185A, the processing circuitry 180 acquires a plurality of parameters, such as parameters input by a user or parameters set by default in the ultrasonic diagnosis apparatus 1, and three-dimensional data. The parameters include, for example, opacity parameters, base color parameters, and rendering parameters. These parameters will be described later in detail.

The opacity curve generation function 185B is a function of generating an opacity curve. The opacity curve is a graph formed by correlating an echo reflection intensity and an opacity value. The opacity value is a value representing the degree of opacity, for example, ranging from "0" to "1". For example, the opacity value "0" represents transparency and the opacity value "1" represents opacity.

By the opacity curve generation function 185B, the processing circuitry 180 generates an opacity curve based on the opacity parameters. The opacity parameters include, for example, a transfer function that defines the shape of the opacity curve and a threshold value defining a boundary of the transparency or the opacity. The transfer function may be either linear or nonlinear. A plurality of threshold values may be provided; for example, two boundaries for the transparency and the opacity may be defined. In this embodiment, the graph of the opacity curve is expressed as a look up table (LUT), which is used in processing described later. The processing by the opacity curve generation function 185B may be referred to as opacity curve generation processing.

The color attenuation curve generation function 185O is a function of generating a color attenuation curve. The color attenuation curve is a graph formed by correlating an opacity value and a value of color attenuation. The value of color attenuation is a value representing to what extent a base color can be attenuated taking account of propagation of light, and provided for each element of a color expression form. In other words, the color attenuation curve is provided for each element of the color expression form. In this embodiment, RGB is used as the color expression form. The color expression form is not limited to RGB, but may be a color space (for example, HSV and HLS) expressed by three components of a hue, chroma, and lightness (or brightness), or a color space (for example, YUV, YCbCr, and YPbPr) expressed by a brightness signal Y and two color-difference signals.

By the color attenuation curve generation function 185C, the processing circuitry 180 generates the color attenuation curve based on the base color parameters and the opacity curve. The base color parameters include, for example, a combination of RGB (color map) representing a target to be displayed (material). The base color may be read as a reflected color, which is a color reflected from an object. Of the color attenuation curves of a plurality of elements, at least one has a different shape from the others. Therefore, the number of the transfer functions that define the color attenuation curves are two or more. The transfer functions may be either linear or nonlinear. In other words, the processing circuitry 180 generates a color attenuation curve for each element of the color expression form using at least two different transfer functions. In this embodiment, the graph of the color attenuation curve is expressed as a LUT, which is used in processing described later. The processing by the color attenuation curve generation function 185C may be referred to as color attenuation curve generation processing.

The optical property map generation function 185D is a function of generating an optical property map. The optical property map is obtained by converting physical phenomena (for example, color attenuation) assumed to occur when the material is irradiated with light into numerical values, and storing them in a voxel located in a three-dimensional space. In this embodiment, a photon map is generated as an optical property map by using a photon mapping method (described later).

A photon mentioned above is a discrete element that is defined as transferring optical energy in unit time in the photon mapping method to represent light with a computer. In the photon mapping method, collision of photons of the number preset in a system or of the number set by the user is calculated in three-dimensional data and the calculated data are arranged in a scene. The scene is a three-dimensional space in which the optical property map is created.

By the optical property map generation function 185D, the processing circuitry 180 generates an optical property map based on the opacity curve, the color attenuation curve, the rendering parameters, and the three-dimensional data. The rendering parameters include, for example, information on the position of the light source with respect to the material. The processing by the optical property map generation function 185D may be referred to as optical property map generation processing.

The rendering function 185E is a function of generating a rendering image. The rendering images include, for example, a volume rendering image and a global illumination image. In this embodiment, a rendering image not taking a light source into account is defined as a volume rendering image, and a rendering image taking a light source into account is defined as a global illumination image.

The volume rendering image is obtained by volume-rendering volume data. In the volume rendering, luminance and color displayed in each voxel is set in accordance with the brightness value (the brightness value of volume data) allocated to the voxel of the volume data. Further, the volume rendering displays a projection image obtained by projection on the voxel from an arbitrary viewpoint.

On the other hand, the global illumination image is obtained by rendering processing by means of the photon map described above. For the rendering processing, for example, ray tracing is used. In this embodiment, the global illumination image is generated as the rendering image.

By the rendering function 185E, the processing circuitry 180 generates the global illumination image based on the opacity curve, the base color parameters, the rendering parameters, the optical property map, and the three-dimensional image. The rendering parameters include, for example, information on the position of a viewpoint. The processing by the rendering function 185E may be referred to as global illumination rendering processing.

The display control function 186 is a function of causing a display as the output device 103 to display images based on various kinds of ultrasonic image data generated by the image generation function 183. Specifically, for example, by the display control function 186, the processing circuitry 180 controls the display of an image based on the B-mode image data, the Doppler image data, or image data including both generated by the image generation function 183.

More specifically, by the display control function 186, the processing circuitry 180 converts (scan-converts) a scanning line signal sequence of ultrasonic scanning into, for example, a scanning line signal sequence in a video format representatively used by television, etc. to generate display image data. The processing circuitry 180 may also perform various types of processing, such as correction of the dynamic range, brightness, contrast, and γ curve, and an RGB conversion, on the display image data. The processing circuitry 180 may also add supplementary information, such as textual information of various parameters, a scale, or a body mark, to the display image data. The processing circuitry 180 may also generate a user interface (graphical user interface (GUI) to allow the operator to input various instructions through the input device, and cause the display to display the GUI.

Furthermore, by the display control function 186, the processing circuitry 180 may display the global illumination image (GI image) generated by the rendering function 185E. The processing circuitry 180 may display a GUI related to setting of the GI image together with the GI image. Accordingly, the user can change the GI image to a desired display in real time by changing the parameters displayed on the GUI. The parameters that the user can change are, for example, the opacity parameters, the base color parameters, and the rendering parameters.

The system control function 187 is a function of integrally controlling the overall operations of the ultrasonic diagnosis apparatus 1. For example, in the system control function 187, the processing circuitry 180 controls the ultrasound transmission circuitry 110 and the ultrasound reception circuitry 120 based on parameters relating to transmission and reception of ultrasonic waves.

A configuration of the ultrasonic diagnosis apparatus 1 of the first embodiment has been described. Next, an outline and an operation of global illumination image generation processing according to the first embodiment will be described.

Figure 2:
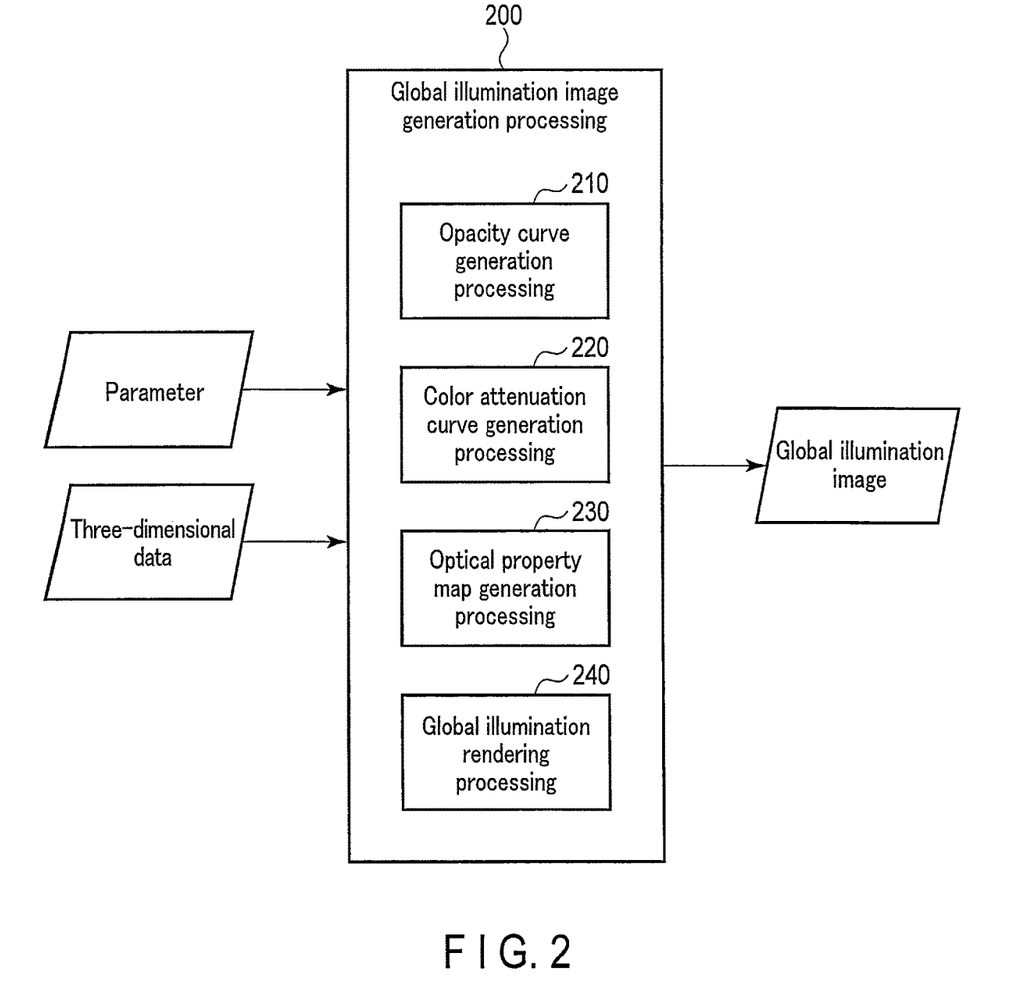
FIG. 2 is a block diagram for explaining an outline of global illumination image generation processing according to the first embodiment.

FIG. 2 is a block diagram for explaining an outline of global illumination image generation processing according to the first embodiment. The processing circuitry 180 performs the global illumination image generation processing 200 based on the acquired parameters and three-dimensional data, thereby generating a global illumination image. The global illumination image generation processing 200 includes, for example, opacity curve generation processing 210, color attenuation curve generation processing 220, optical property map generation processing 230, and global illumination rendering processing 240. If the user does not set parameters relating to the opacity curve generation processing 210 and the color attenuation curve generation processing 220, an opacity curve and a color attenuation curve may be generated from default parameters.

Figure 3:
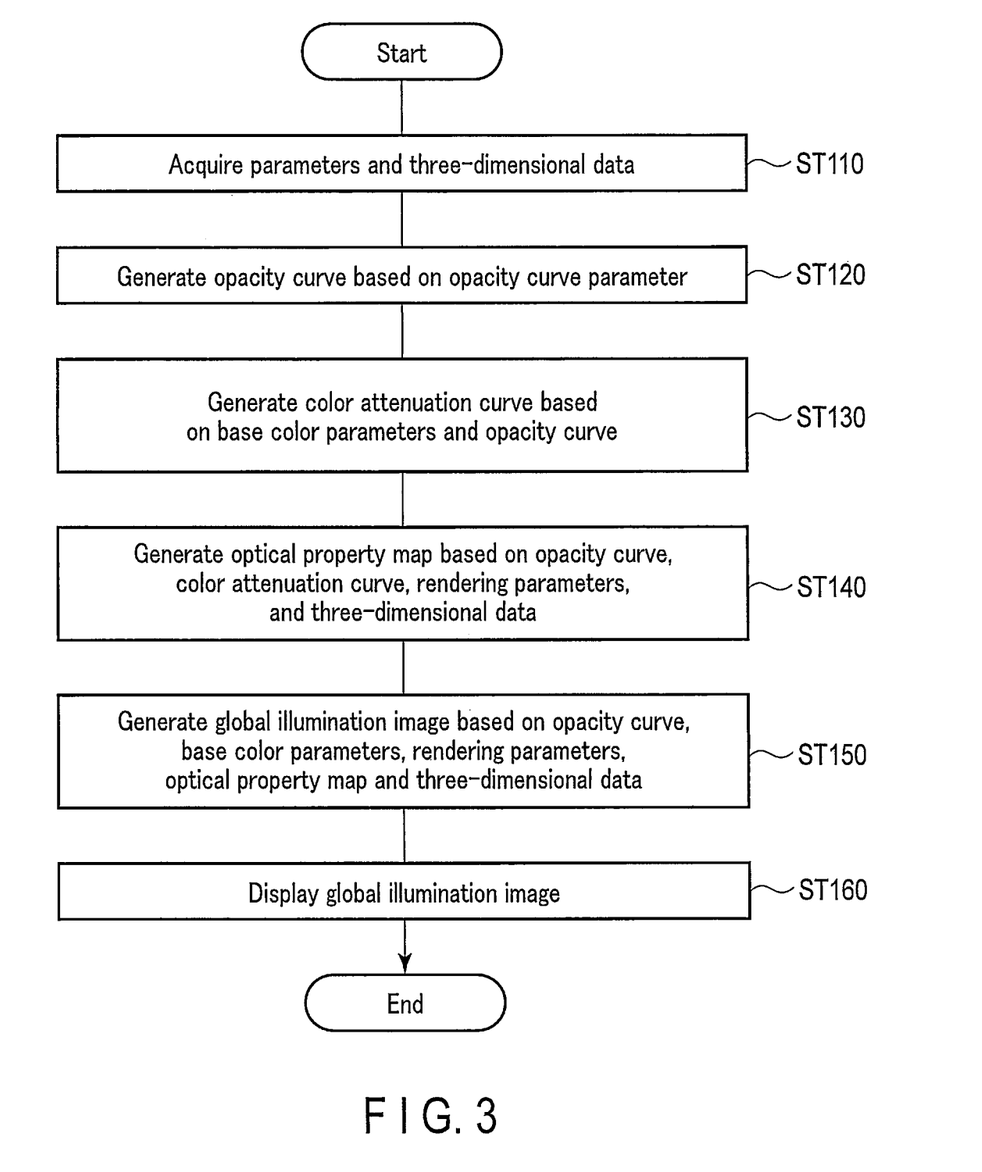
FIG. 3 is a flowchart illustrating an operation of processing circuitry that performs the global illumination image generation processing according to the first embodiment.

FIG. 3 is a flowchart illustrating an operation of processing circuitry that performs the global illumination image generation processing according to the first embodiment. The global illumination image generation processing shown in FIG. 3 is commenced by the user executing, for example, a mode for displaying a global illumination image (illumination mode). The flowchart of FIG. 3 explains processing for one frame.

(Step ST110)

When the global illumination image generation processing is commenced, the processing circuitry 180 executes the acquisition function 185A. When executing the acquisition function 185A, the processing circuitry 180 acquires parameters and three-dimensional data. The parameters include at least one of a parameter input by the user and a parameter set by default in the ultrasonic diagnosis apparatus 1. The three-dimensional data is generated by the three-dimensional data generation function 184 based on the echo reflection intensity acquired in real time by the ultrasonic probe 101.

(Step ST120)

After acquiring the parameters and the three-dimensional data, the processing circuitry 180 executes the opacity curve generation function 185B. When executing the opacity curve generation function 185B, the processing circuitry 180 generates an opacity curve based on the opacity curve parameter. In the following, the opacity curve generation processing by the opacity curve generation function 185B will be described with reference to FIG. 4.

Figure 4:
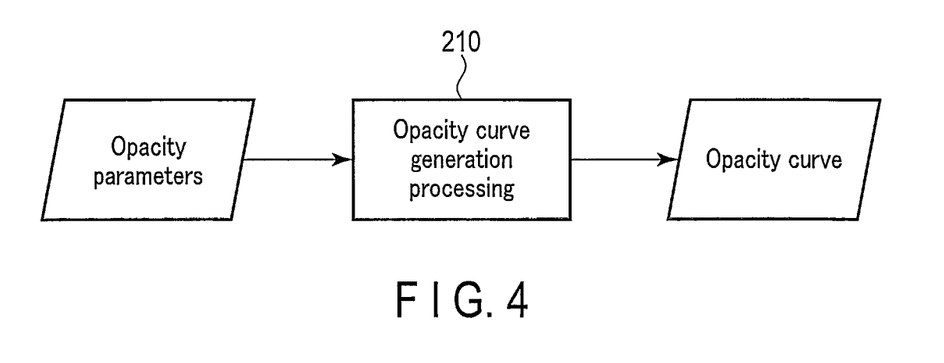
FIG. 4 is a block diagram for explaining opacity curve generation processing shown in FIG. 2.

FIG. 4 is a block diagram for explaining opacity curve generation processing shown in FIG. 2. The processing circuitry 180 performs the opacity curve generation processing 210 on the opacity parameters, thereby generating an opacity curve. Specifically, the opacity curve generation processing 210 generates a LUT relating to an opacity curve based on the echo reflection intensity as a key, using the transfer functions and the threshold values included in the opacity parameters. The processing circuitry 180 calculates a value of the opacity curve LUT by, for example, the following formula (1), $$\text{Opacity } [I] = \begin{cases} C_{trans} \cdot (I - I_{th}) & (\text{if } I > I_{th}) \\ 0 & (\text{if } I \leq I_{th}) \end{cases} \quad (1)$$

In Formula 1, I represents a value of echo reflection intensity. Opacity [I] represents an opacity value (a value of the degree of opacity). $C_{trans}$ represents a transfer function. Lth represents a threshold value defining a boundary of transparency. The value I of echo reflection intensity ranges from 0 to 255 if it is expressed in 8 bits.

(Step ST130)

After generating the opacity curve, the processing circuitry 180 executes the color attenuation curve generation function 185C. When executing the color attenuation curve generation function 185C, the processing circuitry 180 generates a color attenuation curve based on the base color parameters and the opacity curve. The base color parameters are set based on a preset color map or a color map designated by the user. In the following, the color attenuation curve generation processing by the color attenuation curve generation function 185C will be described with reference to FIG. 5.

Figure 5:
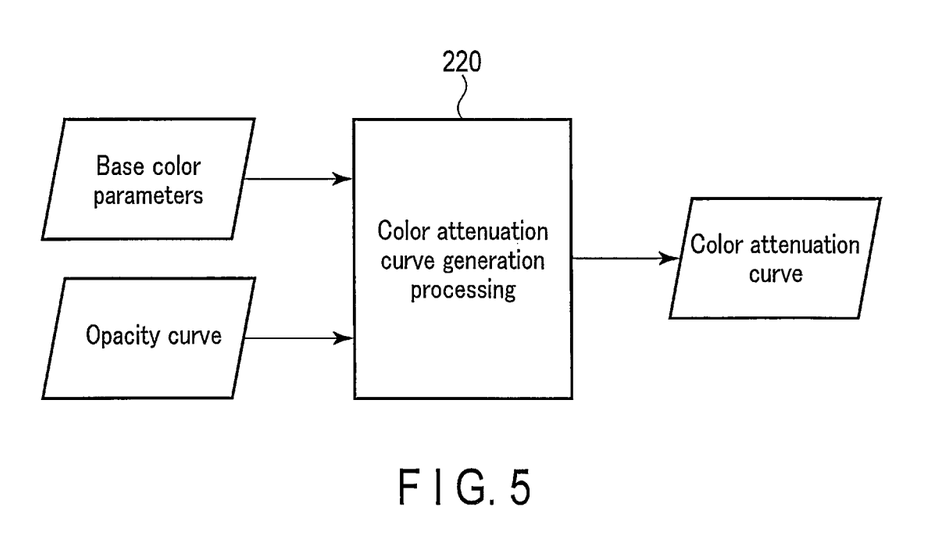
FIG. 5 is a block diagram for explaining color attenuation curve generation processing shown in FIG. 2.

FIG. 5 is a block diagram for explaining the color attenuation curve generation processing shown in FIG. 2. The processing circuitry 180 performs the color attenuation curve generation processing 220 on the base color parameters and the opacity curve, thereby generating a color attenuation curve. Specifically, the color attenuation curve generation processing 220 creates a LUT relating to the color attenuation curve using the opacity value as a key for each of RGB included in the base color parameters. The processing circuitry 180 calculates values of the color attenuation curve LUT respectively corresponding to RGB by, for example, the following formulas (2) to (4):

$$\text{Extinction } [I][R] = \begin{cases} Er/\text{Opacity } [I] & (\text{if Opacity } [I] > 0) \\ 1.0 & (\text{if Opacity } [I] = 0) \end{cases} \quad (2)$$

$$\text{Extinction } [I][G] = \begin{cases} Eg/(\text{Opacity } [I] \cdot \text{Opacity } [I] & (\text{if Opacity } [I] > 0) \\ 1.0 & (\text{if Opacity } [I] = 0) \end{cases} \quad (3)$$

$$\text{Extinction } [I][B] = \begin{cases} Eb/(\text{Opacity } [I] \cdot \text{Opacity } [I] & (\text{if Opacity } [I] > 0) \\ 1.0 & (\text{if Opacity } [I] = 0) \end{cases} \quad (4)$$

In formulas (2) to (4), Extinction[I] [R] represents a value of color attenuation relating to a red (R) element. Similarly, Extinction[I] [G] represents a value of color attenuation relating to a green (G) element, and Extinction[I] [B] represents a value of color attenuation relating to a blue (B) element. Er, Eg, and Eb respectively represent numerical values of R, G, and B elements. The numerical values of the elements are expressed in a floating-point format. For example, if each of the R, G, and B elements is expressed in 8 bits, the numerical values from "0" to "255" are associated with "0" to "1.0". The values of color attenuation are also expressed in the floating-point format.

If Opacity[I] is greater than 0, the calculation of Extinction [I] [R] is different from those of Extinction [I] [G] and Extinction [I] [B]. Specifically, Extinction[I] [R] has a smaller decrease ratio of numerical values as compared to Extinction[I] [G] and Extinction [I] [B]. This means that the color attenuation curves have different shapes.

(Step ST140)

After generating the color attenuation curve, the processing circuitry 180 executes the optical property map generation function 185D. When executing the optical property map generation function 185D, the processing circuitry 180 generates an optical property map based on the opacity curve, the color attenuation curve, the rendering parameters, and the three-dimensional data. In the following, the optical property map generation processing by the optical property map generation function 185D will be described with reference to FIG. 6.

Figure 6:
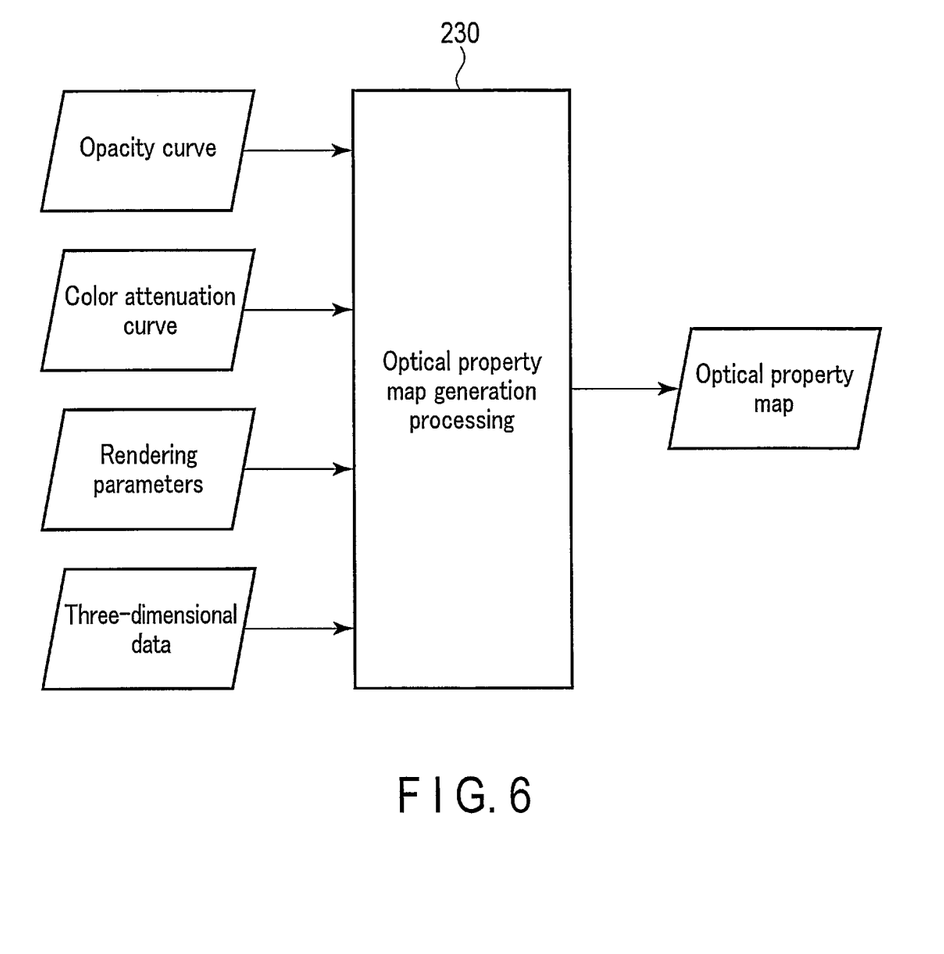
FIG. 6 is a block diagram for explaining optical property map generation processing shown in FIG. 2.

FIG. 6 is a block diagram for explaining the optical property map generation processing shown in FIG. 2. The processing circuitry 180 generates an optical property map by performing the optical property map generation processing on the opacity curve, the color attenuation curve, the rendering parameters, and the three-dimensional data. Specifically, the optical property map generation processing 230 generates a photon map using information on the position of the light source included in the rendering parameters and the three-dimensional data with the photon mapping method.

Various parameters can be set for each photon in the photon map. In this embodiment, the values of color attenuation of R, G, and B are respectively allocated to photons. Specifically, the processing circuitry 180 reads an opacity value and a value of color attenuation based on the echo reflection intensity included in a voxel of the three-dimensional data corresponding to the position of the scene where the photon is located, the opacity curve LUT, and the color attenuation curve LUT. Thereafter, the processing circuitry 180 allocates the value of color attenuation to each photon.

(Step ST150)

After generating the optical property map, the processing circuitry 180 executes the rendering function 185E. When executing the rendering function 185E, the processing circuitry 180 generates a global illumination image based on the opacity curve, the base color parameters, the rendering parameters, the optical property map, and the three-dimensional data. In the following, the global illumination rendering processing by the rendering function 185E will be described with reference to FIG. 7.

Figure 7:
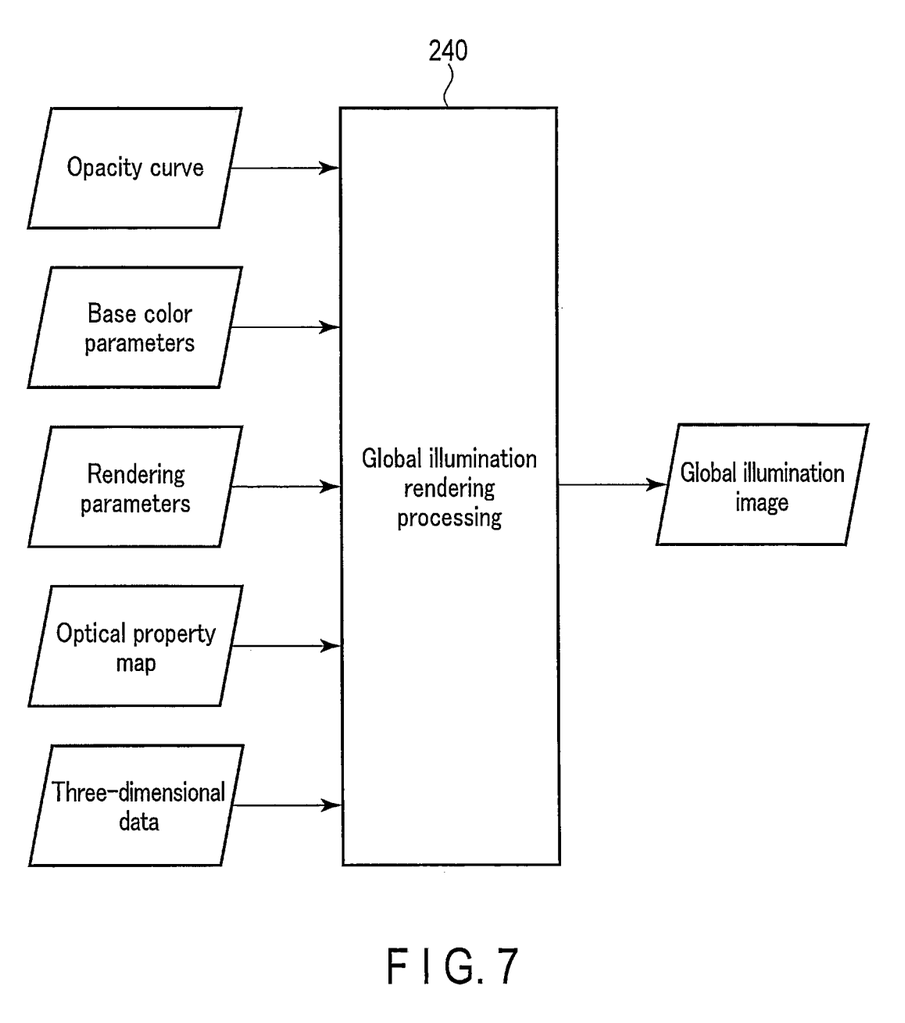
FIG. 7 is a block diagram for explaining global illumination rendering processing shown in FIG. 2.

FIG. 7 is a block diagram for explaining global illumination rendering processing shown in FIG. 2. The processing circuitry 180 performs the global illumination rendering processing 240 on the opacity curve, the base color parameters, the rendering parameters, the optical property map, and the three-dimensional data, thereby generating a global illumination image. Specifically, the global illumination rendering processing 240 generates a projection image (global illumination image) projecting a voxel of three-dimensional data, to which the photon map is applied, from the information on the position of a viewpoint included in the rendering parameters. In the voxel on a projection surface, an opacity value and a base color based on the echo reflection intensity are set.

A display color of the global illumination image is calculated by applying the value of color attenuation included in the photon map to a numerical value of each of R, G, and B elements included in the base color parameters. When the value of color attenuation is calculated from the formulas (2) to (4) indicated above, the display color attenuates more greatly in G and B as compared to R. Therefore, in a place where light attenuates, such as a shadowed area, large parts of R components will remain. In other words, the hue changes in accordance with the echo reflection intensity. (Step ST160)

After generating the global illumination image, the processing circuitry 180 causes the display as the output device 103 to display the global illumination image by the display control function 186. After step ST160, the global illumination image generation processing terminates.

The processing of FIG. 3 may be repeated until the user ends the illumination mode or changes the illumination mode to another mode.

Figure 8:
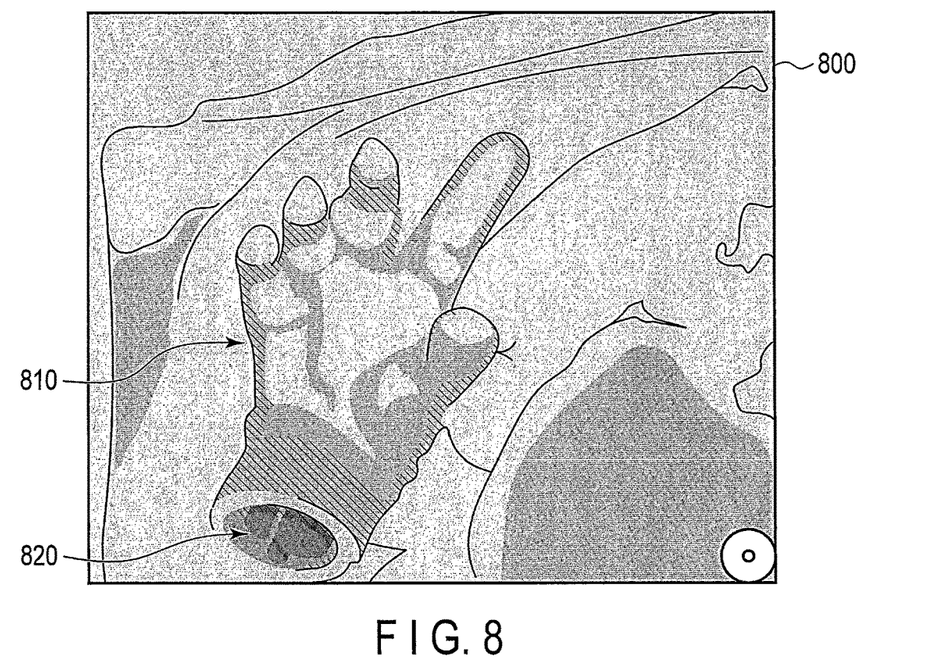
FIG. 8 is a diagram showing a global illumination image obtained when a light source is located in front of a target according to the first embodiment.

FIG. 8 is a diagram showing a global illumination image obtained when a light source is located in front of a target according to the first embodiment. In FIG. 8, since the viewpoint is also located in front of the target, the light emitted from the light source travels in the same direction as the direction of the line of sight. In the global illumination image 800 of FIG. 8, changes of the hue are expressed with a gray scale, and shadowed areas are expressed with hatching. This also applies to the global illumination images described below.

The global illumination image 800 in FIG. 8 illustrates the right hand of an embryo. When focusing on a palm portion 810 of the right hand, there is a change in hue in a portion different from the shadowed areas. As a result, the shape of the palm in the palm portion 810 is clear. When focusing on a cross sectional portion 820 of the right hand, there is a change in hue as in the palm portion 810; therefore, the shape of a structure (for example, a bone) can be clearly recognized. On the other hand, according to the conventional method, such a change in hue does not occur. An image according to the conventional art will be described with reference to the FIG. 11.

Figure 11:
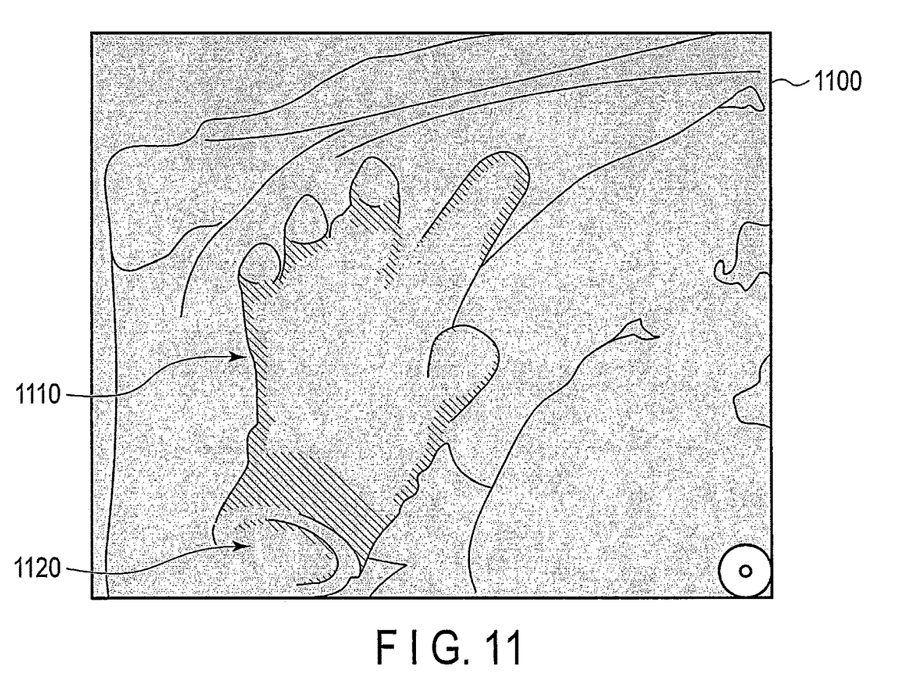
FIG. 11 is a diagram showing a global illumination image obtained when a light source is located in front of a target according to the conventional art.

FIG. 11 is a diagram showing a global illumination image obtained when a light source is located in front of a target according to the conventional art. The global illumination image 1100 in FIG. 11 illustrates the right hand of an embryo as the global illumination image 800. When focusing on a palm portion 1110 of the right hand, there is no change in hue, although shadowed areas are expressed. Accordingly, the shape of the palm is not clear. When focusing on a cross sectional portion 1120 of the right hand, there is also no change in hue as in the palm portion 1110; therefore, the shape of a structure cannot be clearly recognized.

Figure 9:
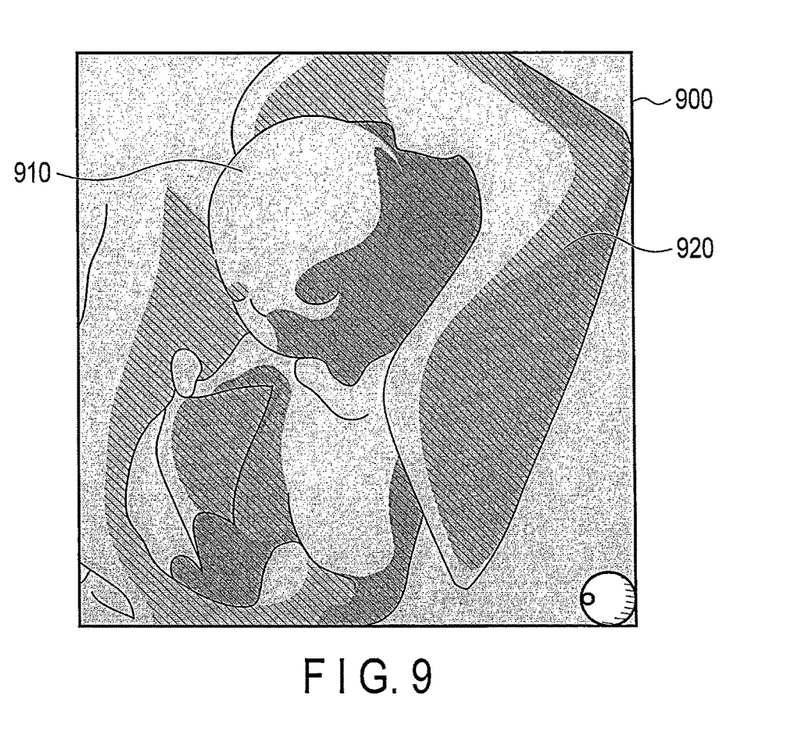
FIG. 9 is a diagram showing a global illumination image obtained when a light source is located on a left side of a target according to the first embodiment.

FIG. 9 is a diagram showing a global illumination image obtained when a light source is located on a left side of a target according to the first embodiment. In FIG. 9, since the viewpoint is located in front of the target, the light emitted from the light source travels from left to right with respect to the direction of the line of sight.

The global illumination image 900 in FIG. 9 illustrates the whole body of an embryo. When focusing on a head portion 910 of the embryo, the left side of the face is shadowed and the outline of the face is unclear. When focusing on a structure 920 other than the embryo, the boundary can be recognized in accordance with a change in hue. In contrast, according to the conventional method, since the outline is emphasized, the view may be unnatural. An image according to the conventional art will be described with reference to the FIG. 12.

Figure 12:
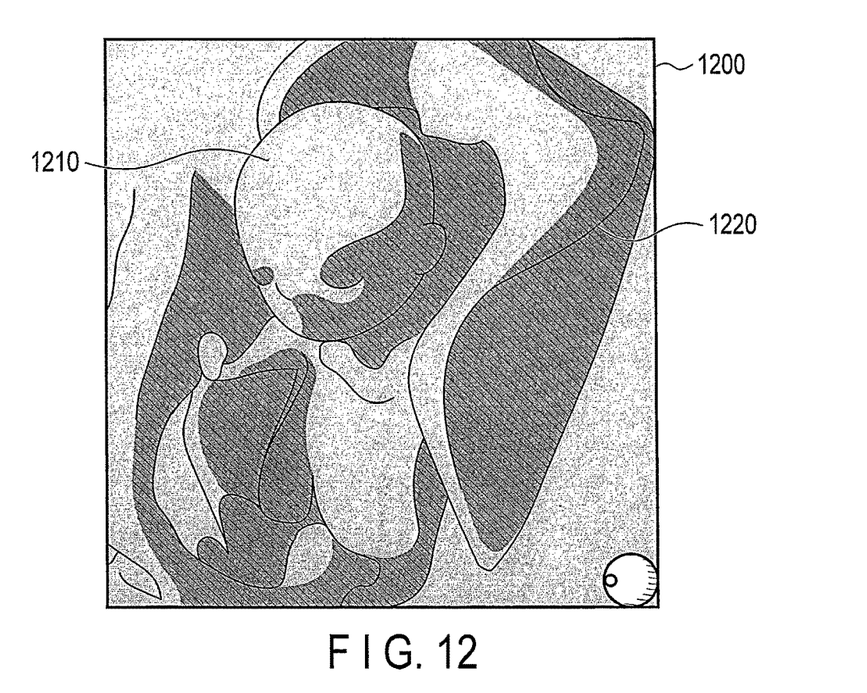
FIG. 12 is a diagram showing a global illumination image obtained when a light source is located on a left side of a target according to the conventional art.

FIG. 12 is a diagram showing a global illumination image obtained when the light source is located on a left side of a target according to the conventional art. A global illumination image 1200 in FIG. 12 illustrates the whole body of an embryo as the global illumination image 900. When focusing on a head portion 1210 of the embryo, outlines of the left temporal region, the left cheek, and the left ear are clearly drawn as edges, and the view is unnatural. When focusing on a structure 1220 other than the embryo, although the structure is a smooth region, edges of the structure are drawn as in the head portion 1210.

In summary, according to the ultrasonic diagnosis apparatus of the first embodiment, when generating a global illumination image, the degree of color attenuation is associated with the echo reflection intensity, and the reflected color is set as a single color which is not associated with the echo reflection intensity. Furthermore, in the ultrasonic diagnosis apparatus, the color attenuation curve that defines the degree of color attenuation is associated with the opacity curve, such that the higher the echo, the more color is transmitted, and the lower the echo, the less color is transmitted. Accordingly, in the generated global illumination image, not only a gray scale of a simple color but also RGB values change in a boundary where the echo reflection intensity changes greatly. Therefore, the boundary portion is illustrated as a change in color and can be recognized as a natural outline. On the other hand, since the shadow portions, caused by the way the light hits the image, namely the position of the light source, are depicted as in the conventional method, the reality of a change in shadows is maintained. Therefore, the ultrasonic diagnosis apparatus of the embodiment can produce an effect that satisfies the improvement in both the reality and the visibility as compared to the conventional method with a calculation load equivalent to that using color attenuation and reflected color in the conventional method.

As has been described above, the ultrasonic diagnosis apparatus according to the first embodiment generates three-dimensional data based on an echo reflection intensity acquired through the probe, acquires a plurality of parameters including base color parameters, and three-dimensional data; and generates a rendering image of the three-dimensional data using a value of color attenuation taking account of propagation of light based on the echo reflection intensity and using the base color parameters.

Therefore, the ultrasonic diagnosis apparatus according to the first embodiment can generate a natural rendering image without increasing the calculation load by associating the color attenuation with the echo reflection intensity. Since the calculation load is the same as that in the case where the color attenuation is not associated with the echo reflection intensity, a natural outline can be drawn at an end of a structure without impairing the real-time display. Furthermore, since a color variance of an ultrasonic image due to a characteristic of speckle does not occur at the end of the structure, hues of a plurality of colors overlap, thereby producing an effect similar to actual color unevenness, so that a smooth portion of the structure can be seen more naturally.

Second Embodiment

In the first embodiment, a plurality of functions relating to the global illumination image generation processing have been described. In a second embodiment, an image processing apparatus having the functions mentioned above will be described.

Figure 10:
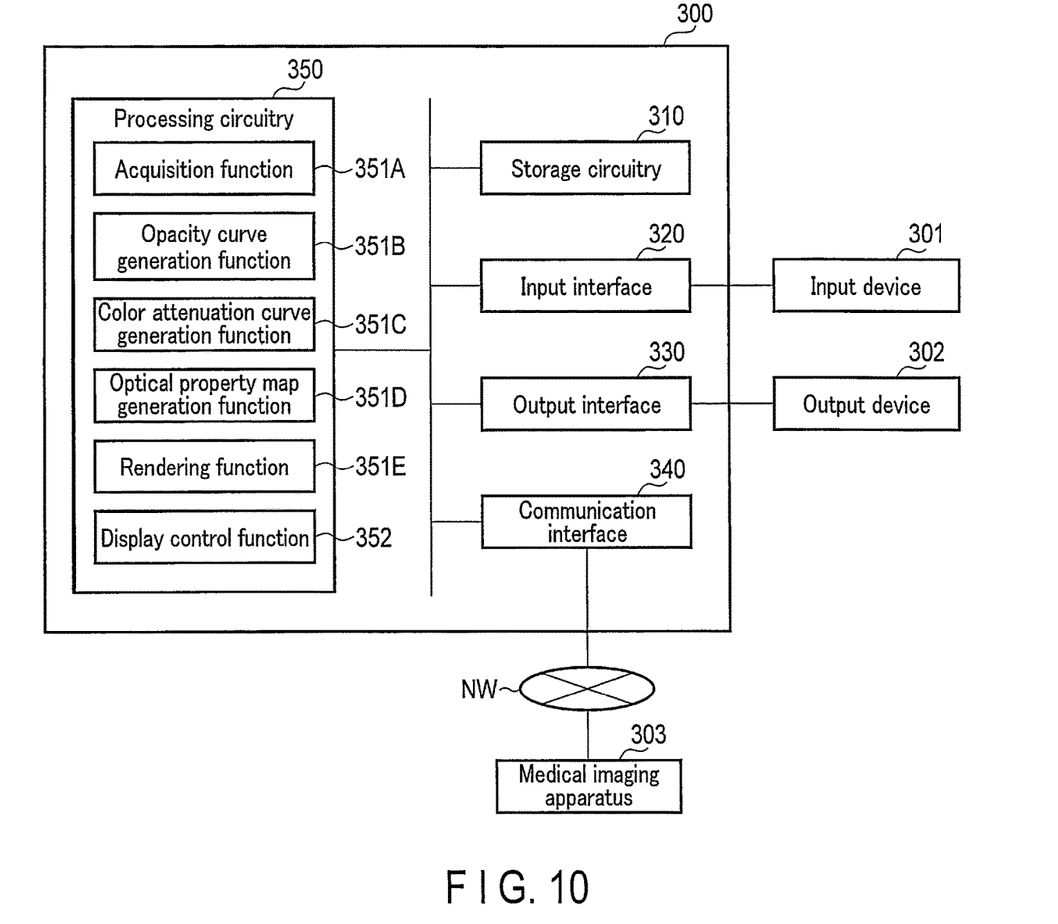
FIG. 10 is a block diagram showing a configuration example of an image processing apparatus according to a second embodiment.

FIG. 10 is a block diagram showing a configuration example of the image processing apparatus according to the second embodiment. An image processing apparatus 300 shown in FIG. 10 is connected to an input device 301 and an output device 302. The image processing apparatus 300 is connected to a medical imaging apparatus 303 via a network NW. The medical imaging apparatus 303 corresponds to, for example, an ultrasonic diagnosis apparatus. The input device 301 and the output device 302 are substantially the same as the input device 102 and the output device 103 shown in FIG. 1.

The image processing apparatus 300 is an apparatus that performs the global illumination image generation processing to generate a global illumination image. The image processing apparatus 300 includes storage circuitry 310, an input interface 320, an output interface 330, a communication interface 340, and processing circuitry 350.

The storage circuitry 310 includes a processor-readable storage medium, such as a magnetic storage medium, an optical storage medium, or a semiconductor memory. The storage circuitry 310 stores programs relating to the global illumination image generation processing, various data, etc. The programs and various data may be pre-stored in the storage circuitry 310. Alternatively, the program and data may be stored and distributed in a non-transitory storage medium, read from the non-transitory storage medium and installed in the storage circuitry 310. The storage circuitry 310 stores B-mode image data, contrast image data, image data relating to bloodstream visualization, three-dimensional data, etc. generated at the medical imaging apparatus 303, in accordance with an operation that is input via the input interface 320.

The storage circuitry 310 may be a drive etc. which reads and writes various types of information to and from a portable storage medium, such as a CD drive, a DVD drive, and a flash memory. The storage circuitry 310 may write the stored data onto a portable storage medium to store the data into an external device by way of the portable storage medium.

The input interface 320 receives various instructions from the operator through the input device 301. The input device 301 is, for example, a mouse, a keyboard, a panel switch, a slider switch, a trackball, a rotary encoder, an operation panel, or a touch panel. The input interface 320 is connected to the processing circuitry 350 via a bus, for example, so that it can convert an operation instruction that is input by the operator into an electric signal, and output the electric signal to the processing circuitry 350. The input interface 320 is not limited to physical operation components such as a mouse and a keyboard. Examples of the input interface may include a circuit configured to receive an electric signal corresponding to an operation instruction that is input from an external input device provided separately from the image processing apparatus 300 and to output this electric signal to the processing circuitry 350.

The output interface 330 is an interface to output, for example, the electric signal from the processing circuitry 350 to the output device 302. The output device 302 may be any display such as a liquid crystal display, an organic EL display, an LED display, a plasma display, or a CRT display. The output device 302 may be a touch-panel display that also serves as the input device 301. The output device 302 may also include a speaker configured to output a voice in addition to the display. The output interface 330 is connected to the processing circuitry 350, for example, via a bus, and outputs the electric signal from the processing circuitry 350 to the output device 302.

The communication interface 340 is connected to the medical imaging apparatus 303 via, for example, the network NW, and performs data communication with the medical imaging apparatus 303.

The processing circuitry 350 is a processor acting as a nerve center of the image processing apparatus 300, for example. The processing circuitry 350 executes the programs stored in the storage circuitry 310, thereby realizing the functions corresponding to the programs. The processing circuitry 350 has, for example, an acquisition function 351A (acquisition portion), an opacity curve generation function 351B, a color attenuation curve generation function 351C (color attenuation curve generation portion), an optical property map generation function 351D (optical property map generation portion), a rendering function 351E (rendering portion), and a display control function 352 (display control portion).

The acquisition function 351A is a function for acquiring data relating to GI image generation processing. Specifically, by the acquisition function 351A, the processing circuitry 350 acquires parameters input by the user, parameters set by default in the image processing apparatus 300, and three-dimensional data from the medical imaging apparatus 303.

The opacity curve generation function 351B, the color attenuation curve generation function 351C, the optical property map generation function 351D, the rendering function 351E, the display control function 352 are, for example, respectively the same as the opacity curve generation function 185B, the color attenuation curve generation function 185C, the optical property map generation function 185D, the rendering function 185E and the display control function 186 of the first embodiment.

Thus, an effect similar to that obtained by the first embodiment can be expected from the image processing apparatus according to the second embodiment.

According to at least one of the embodiments described above, a natural rendering image can be generated without increasing the calculation load.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the foregoing embodiments, the following matters are disclosed as one aspect and a selective feature of the present invention.

(1) An ultrasonic diagnosis apparatus, comprises processing circuitry configured to:
   generate three-dimensional data based on an echo reflection intensity acquired through a probe;
   acquire a plurality of parameters including base color parameters, and the three-dimensional data; and
   generate a rendering image of the three-dimensional data using a value of color attenuation taking account of propagation of light based on the echo reflection intensity and using the base color parameters.

(2) An image processing apparatus, comprises processing circuitry configured to:
   acquire a plurality of parameters including base color parameters, and three-dimensional data generated based on an echo reflection intensity acquired through a probe; and
   generate a rendering image of the three-dimensional data using a value of color attenuation taking account of propagation of light based on the echo reflection intensity and using the base color parameters.

(3) The processing circuitry may generate a color attenuation curve, defined by associating an opacity value and the value of color attenuation, based on the base color parameters and an opacity curve defined by associating the echo reflection intensity and the opacity value, and the value of color attenuation is calculated based on the echo reflection intensity, the opacity curve, and the color attenuation curve.

(4) The plurality of parameters may further include rendering parameters including information of a position of a light source directed to a target, the rendering parameters further include information of a position of a viewpoint, and the processing circuitry may
   generate an optical property map storing the value of color attenuation based on the opacity curve, the color attenuation curve, the rendering parameters, and the three-dimensional data; and
   generate the rendering image based on the opacity curve, the base color parameters, the rendering parameters, the optical property map, and the three-dimensional data.

(5) The processing circuitry may generate the optical property map using a photon mapping method.

(6) The value of color attenuation may include at least one of a value of extinction color and a value of a color transmission.

(7) The color attenuation curve may be provided for each element of color expression form.

(8) The color expression form may one of RGB, HSV, HLS, YUV, YCrCb, and YPbPr.

(9) The processing circuitry may generate the color attenuation curve for each element of the color expression form using at least two different transfer functions.

(10) The processing circuitry may generate the rendering image by executing global illumination rendering processing.

(11) The base color parameters may set based on a preset color map or a color map designated by a user.

(12) The processing circuitry may generate the rendering image, such that the higher the echo, the more color is transmitted, and the lower the echo, the less color is transmitted.

(13) The color attenuation curve is a curve such that the higher the echo, the more color is transmitted, and the lower the echo, the less color is transmitted.

(14) A method comprises:
   acquiring a plurality of parameters including base color parameters, and three-dimensional data generated based on an echo reflection intensity acquired through a probe; and
   generating a rendering image of the three-dimensional data using a value of color attenuation taking account of propagation of light based on the echo reflection intensity and using the base color parameters.

(15) A non-transitory computer-readable storage medium storing a program for causing a computer to execute processing comprises:
   acquiring a plurality of parameters including base color parameters, and three-dimensional data generated based on an echo reflection intensity acquired through a probe; and
   generating a rendering image of the three-dimensional data using a value of color attenuation taking account of propagation of light based on the echo reflection intensity and using the base color parameters.

(16) The program may cause the computer to further execute generating a color attenuation curve, defined by associating an opacity value and the value of color attenuation, based on the base color parameters and an opacity curve defined by associating the echo reflection intensity and the opacity value, and the value of color attenuation is calculated based on the echo reflection intensity, the opacity curve, and the color attenuation curve.

(17) The plurality of parameters may further include rendering parameters including information of a position of a light source directed to a target, the rendering parameters further include information of a position of a viewpoint, and the program may cause the computer to further execute:
   generating an optical property map storing the value of color attenuation based on the opacity curve, the color attenuation curve, the rendering parameters, and the three-dimensional data; and
   generating the rendering image based on the opacity curve, the base color parameters, the rendering parameters, the optical property map, and the three-dimensional data.

(18) The program may cause the computer to further execute generating the optical property map using a photon mapping method.

(19) The value of color attenuation may include at least one of a value of extinction color and a value of a color transmission.

(20) The color attenuation curve may be provided for each element of color expression form.

(21) The color expression form may one of RGB, HSV, HLS, YUV, YCrCb, and YPbPr.

(22) The program may cause the computer to further execute generating the color attenuation curve for each element of the color expression form using at least two different transfer functions.

(23) The program may cause the computer to further execute generating the rendering image by executing global illumination rendering processing.

(24) The base color parameters may set based on a preset color map or a color map designated by a user.

(25) The program may cause the computer to further execute generating the rendering image, such that the higher the echo, the more color is transmitted, and the lower the echo, the less color is transmitted.

(26) The color attenuation curve is a curve such that the higher the echo, the more color is transmitted, and the lower the echo, the less color is transmitted.

The invention claimed is:

1. An ultrasonic diagnosis apparatus, comprising:
processing circuitry configured to:
- generate three-dimensional data based on an echo reflection intensity acquired through a probe;
- acquire a plurality of parameters including base color parameters, and the three-dimensional data; and
- generate a rendering image of the three-dimensional data using a value of color attenuation taking account of propagation of light based on the echo reflection intensity and using the base color parameters, wherein the processing circuitry is further configured to generate a color attenuation curve based on the base color parameters and an opacity curve defined by associating the echo reflection intensity and an opacity value, and the value of color attenuation is calculated based on the echo reflection intensity, the opacity curve, and the color attenuation curve.

2. The ultrasonic diagnosis apparatus according to claim 1, wherein the color attenuation curve corresponds to the opacity value and the value of color attenuation.

3. The ultrasonic diagnosis apparatus according to claim 1, wherein the plurality of parameters further include rendering parameters including information of a position of a light source directed to a target, the rendering parameters further include information of a position of a viewpoint, and the processing circuitry is further configured to:
- generate an optical property map storing the value of color attenuation based on the opacity curve, the color attenuation curve, the rendering parameters, and the three-dimensional data; and
- generate the rendering image based on the opacity curve, the base color parameters, the rendering parameters, the optical property map, and the three-dimensional data.

4. The ultrasonic diagnosis apparatus according to claim 3, wherein the processing circuitry is further configured to generate the optical property map using a photon mapping method.

5. The ultrasonic diagnosis apparatus according to claim 1, wherein the color attenuation curve is provided for each element of color expression form.

6. The ultrasonic diagnosis apparatus according to claim 5, wherein the color expression form is one of RGB, HSV, HLS, YUV, YCrCb, and YPbPr.

7. The ultrasonic diagnosis apparatus according to claim 5, wherein the processing circuitry is further configured to generate the color attenuation curve for each element of the color expression form using at least two different transfer functions.

8. The ultrasonic diagnosis apparatus according to claim 1, wherein the processing circuitry is further configured to generate the rendering image by executing global illumination rendering processing.

9. The ultrasonic diagnosis apparatus according to claim 1, wherein the base color parameters are set based on a preset color map or a color map designated by a user.

10. The ultrasonic diagnosis apparatus according to claim 1, wherein the processing circuitry is further configured to generate the rendering image, such that the higher the echo, the more color is transmitted, and the lower the echo, the less color is transmitted.

11. The ultrasonic diagnosis apparatus according to claim 10, wherein the color attenuation curve is a curve such that the higher the echo, the more color is transmitted, and the lower the echo, the less color is transmitted.

12. An image processing apparatus, comprising:
processing circuitry configured to:
- acquire a plurality of parameters, and three-dimensional data generated based on an echo reflection intensity acquired through a probe; and
- generate a rendering image of the three-dimensional data using a value of color attenuation taking account of propagation of light based on the echo reflection intensity and using base color parameters included in the plurality of parameters, wherein the processing circuitry is further configured to generate a color attenuation curve based on the base color parameters and an opacity curve defined by associating the echo reflection intensity and an opacity value, and the value of color attenuation is calculated based on the echo reflection intensity, the opacity curve, and the color attenuation curve.

13. A method comprising:
- acquiring a plurality of parameters including base color parameters, and three-dimensional data generated based on an echo reflection intensity acquired through a probe; and
- generating a rendering image of the three-dimensional data using a value of color attenuation taking account of propagation of light based on the echo reflection intensity and using the base color parameters, wherein
the generating the rendering image comprises generating a color attenuation curve based on the base color parameters and an opacity curve defined by associating the echo reflection intensity and an opacity value, and the value of color attenuation is calculated based on the echo reflection intensity, the opacity curve, and the color attenuation curve.

14. A non-transitory computer-readable storage medium storing a program for causing a computer to execute processing comprising:
- acquiring a plurality of parameters including base color parameters, and three-dimensional data generated based on an echo reflection intensity acquired through a probe; and
- generating a rendering image of the three-dimensional data using a value of color attenuation taking account of propagation of light based on the echo reflection intensity and using the base color parameters, wherein
the generating the rendering image comprises generating a color attenuation curve based on the base color parameters and an opacity curve defined by associating the echo reflection intensity and an opacity value, and the value of color attenuation is calculated based on the echo reflection intensity, the opacity curve, and the color attenuation curve.

* * * * *